United States Patent [19]

Marchi et al.

[11] 4,341,785
[45] Jul. 27, 1982

[54] IMIDAZO-RIFAMYCIN DERIVATIVES WITH ANTIBACTERIAL UTILITY

[75] Inventors: Egidio Marchi; Lauretta Montecchi, both of Casalecchio di Reno, Italy

[73] Assignee: Alfa Farmaceutici S.p.A., Bologna, Italy

[21] Appl. No.: 262,123

[22] Filed: May 11, 1981

[30] Foreign Application Priority Data

May 22, 1980 [IT] Italy ................... 3429 A/80

[51] Int. Cl.$^3$ ................ A61K 31/44; C07D 491/22
[52] U.S. Cl. ..................... 424/256; 260/239.3 P
[58] Field of Search ............. 260/239.3 P; 424/256

[56] References Cited

FOREIGN PATENT DOCUMENTS

| 2739623 | 4/1978 | Fed. Rep. of Germany ... 260/239.3 P |
| 2739671 | 4/1978 | Fed. Rep. of Germany ... 260/239.3 P |
| 2741066 | 4/1978 | Fed. Rep. of Germany ... 260/239.3 P |

OTHER PUBLICATIONS

Derwent Abstract of South African Patent, 68/0903, published July 9, 1968.

*Primary Examiner*—Robert T. Bond
*Attorney, Agent, or Firm*—Bucknam and Archer

[57] ABSTRACT

New rifamicyn derivatives of the following general formula wherein:
A may be the structure —x— is a chemical bond or nil;
R is hydrogen or acetyl
$R_1$ and $R_2$ independently represent hydrogen, ($C_{1-4}$) alkyl, benzyloxy, mono- and di-($C_{1-3}$)alkylamino-($C_{1-4}$)alkyl, ($C_{1-3}$)alkoxy- ($C_{1-4}$)alkyl, hydroxymethyl, hydroxy-($C_{2-4}$)-alkyl, nitro or $R_1$ and $R_2$ taken together with two consecutive carbon atoms of the pyridine nucleus form a benzene ring optionally substituted by one or two methyl or ethyl groups; $R_3$ is a hydrogen atom or nil;

with the proviso that, when A is $A_1$, —x— is nil and $R_3$ is a hydrogen atom; with the further proviso that, when A is $A_2$, —x— is a chemical bond and $R_3$ is nil.

The compounds possess antibacterial utility.

13 Claims, No Drawings

IMIDAZO-RIFAMYCIN DERIVATIVES WITH ANTIBACTERIAL UTILITY

BACKGROUND OF THE INVENTION

Rifamycin derivatives bearing a heterocyclic ring which is condensed at the 3,4-positions are known from the art literature, including the patent literature. As an example, in South African Pat. No. 68/0903 there are claimed pyrrolo [5,4-c] rifamycin SV derivatives, whereas German Patent Publications Nos. 2,739,671 and 2,739,623 describe some imidazo [5,4-c] rifamycin SV compounds which bear substituent at the positions 1 and 2. Thiazolo [5,4-c] rifamycin SV (rifamycin P) derivatives are reported in the German Patent Publication No. 2,741,066.

SUMMARY OF THE INVENTION

The present invention refers to new imidazo-rifamycin derivatives of the following general formula

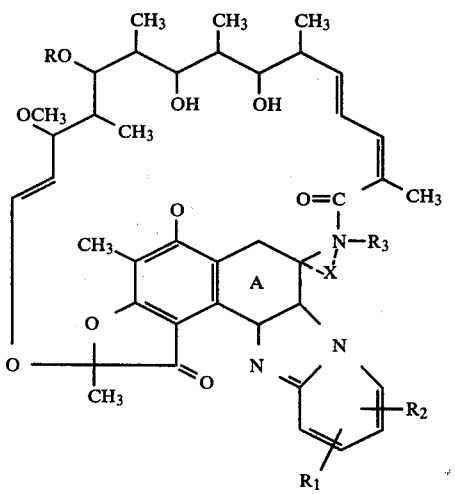

wherein:
A may be the structure

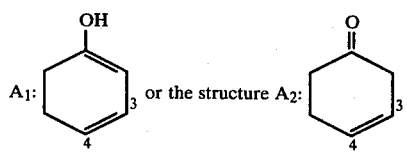

—x— is a chemical bond or nil;
R is hydrogen or acetyl
$R_1$ and $R_2$ independently represent hydrogen, $(C_{1-4})$ alkyl, benzyloxy, mono- and di-$(C_{1-3})$alkylamino-$(C_{1-4})$alkyl, $(C_{1-3})$alkoxy- $(C_{1-4})$alkyl, hydroxymethyl, hydroxy-$(C_{2-4})$-alkyl, nitro or $R_1$ and $R_2$ taken together with two consecutive carbon atoms of the pyridine nucleus form a benzene ring optionally substituted by one or two methyl or ethyl groups; $R_3$ is a hydrogen atom or nil;
with the proviso that, when A is $A_1$, —x— is nil and $R_3$ is a hydrogen atom; with the further proviso that, when A is $A_2$, —x— is a chemical bond and $R_3$ is nil.

The compounds possess antibacterial utility.

A preferred group of compounds comprises those compounds of formula I wherein A may be the structure $A_1$ or the structure $A_2$ as above indicated, —x— is a chemical bond or nil, R is hydrogen or acetyl, $R_1$ and $R_2$ independently represent hydrogen, $(C_{1-4})$alkyl, benzyloxy, hydroxy $(C_{2-4})$ alkyl, di-$(C_{1-3})$ alkylamino-$(C_{1-4})$ alkyl, nitro or $R_1$ and $R_2$ taken together with two consecutive carbon atoms of the pyridine nucleus form a benzene ring and $R_3$ is a hydrogen atom or nil; with the proviso that, when A is $A_1$, —x— is nil and $R_3$ is a hydrogen atom; with the further proviso that, when A is $A_2$, —x— is a chemical bond and $R_3$ is nil.

A second preferred group of compounds comprises those compounds of formula I wherein A may be the structure $A_1$ or the structure $A_2$ as above indicated, —x— is a chemical bond or nil, R is acetyl, $R_1$ and $R_2$ independently represent hydrogen, $(C_{1-4})$ alkyl or $R_1$ and $R_2$ taken together with two consecutive carbon atoms of the pyridine nucleus form a benzene ring and $R_3$ is a hydrogen atom or nil; with the proviso that, when A is $A_1$, —x— is nil and $R_3$ is a hydrogen atom; with the further proviso that, when A is $A_2$, —x— is a chemical bond and $R_3$ is nil.

As used herein the terms $(C_{1-3})$ alkyl, $(C_{2-4})$alkyl and $(C_{1-4})$ alkyl identifies linear or branched alkyl radicals containing from 1 to 3 or 2 to 4 or 1 to 4 carbon atoms, such as, for instance, methyl, ethyl, n-propyl, isopropyl, n-butyl, sec.-butyl, isobutyl or tert.-butyl, whereas the term $(C_{1-3})$ alkoxy essentially refers to methoxy, ethoxy, propoxy or isopropoxy groups.

The compounds of the invention are prepared according to methods which essentially depends on the type of compound one wishes to obtain. Thus, for instance, the compounds of formula I wherein A represents structure $A_2$, R, $R_1$ and $R_2$ are as above defined, —x— is an additional bond and $R_3$ represents nil are conveniently prepared by reacting a 3-halorifamycin S of formula

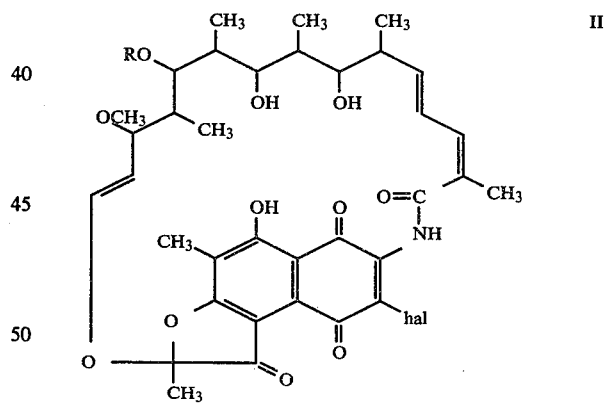

wherein hal represents a halogen atom, preferably bromine or iodine, and R is defined as above, with a compound of formula

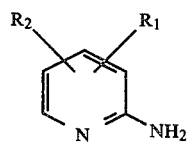

wherein $R_1$ and $R_2$ have the same meaning as before.

In the actual practice, the reaction is carried out by contacting a molar amount of the compound of formula II with a molar excess of the compound of formula III.

This molar excess varies from about 2 to about 8 or more equivalents calculated on the compound of formula II. The reaction is performed in the presence of an inert organic solvent such as, for instance, an aliphatic alkanol containing from 1 to 4 carbon atoms, a lower halogenated hydrocarbon from 1 to 2 carbon atoms, dioxane, tetrahydrofuran or mixture thereof, at a temperature which may vary within wide limits, though the room temperature is the preferred one. The reaction is completed within a period of time comprised between about 1 and about 4 hours.

The so obtained compounds may undergo further chemical reactions having the purpose of preparing other substances falling within the scope of the above formula I. Thus, for instance, compounds of formula I can be obtained where A is structure $A_1$, R, $R_1$ and $R_2$ have the same meanings as before, —x— represents nil and $R_3$ stands for a hydrogen atom, by treating the corresponding substance in which A represents structure $A_2$ with a suitable reducing agent such as, for instance, L(—)-ascorbic acid.

This step, which can even be performed without isolating the compound deriving from the condensation of the starting substances of formula II and III, occurs essentially at room temperature, though a gentle heating can sometimes favor the reaction course, for a period of time varying from about 10 minutes to about 1 hour, in an inert organic solvent again selected, for instance, from an aliphatic alkanol from 1 to 4 carbon atoms, a lower halogenated hydrocarbon from 1 to 2 carbon atoms, dioxane, tetrahydrofuran or mixtures thereof. In turn, the so obtained compounds of formula I wherein A is structure $A_1$, R, $R_1$ and $R_2$ have the above meanings, —x— represents nil and $R_3$ stands for a hydrogen atom, can be transformed into the corresponding products in which A represents structure $A_2$ by treatment with an appropriate oxidizing agent such as, for instance, manganese dioxide, lead tetracetate, dichloro-dicyano-benzoquinone, 2,3,4,5-tetrachloro-benzoquinone, 2,3,5,6-tetrachloro-benzoquinone and analogs. This reaction is carried out in an inert organic solvent like those indicated above, at temperature comprised between room temperature and the boiling temperature of the reaction mixture. A period of time varying from about 10 minutes to about 1 hour is sufficient for having the reaction completed.

Finally, the compounds of formula I wherein R is hydrogen are conveniently prepared by hydrolyzing, under alkaline conditions, the corresponding compounds where R is acetyl. This hydrolysis is carried out in the presence of a solvent, generally an aliphatic alkanol from 1 to 4 carbon atoms, treating a molar amount of the selected compound with a molar excess of an alkali agent, e.g. sodium or potassium hydroxide or carbonate, at room temperature, for a period of time varying from about 1 to about 5 hours. The so obtained compounds of formula I in which R is hydrogen may in turn undergo the above illustrated reduction or oxidation reactions, depending on the structure A represents.

The substances according to the invention are recovered from the reaction medium by means of techniques entirely familiar to a skilled technician. These techniques comprise the extraction with a suitable organic solvent, e.g. ethyl acetate, chloroform, methylene chloride and analogs or mixtures thereof, the evaporation to dryness of the organic extract and taking up the residue with an appropriate solvent from which the final product separates. Alternatively, the reaction mixture can be directly evaporated to dryness and the obtained residue is in turn taken up with a suitable solvent from which the final product separates Crystallization solvents which can advantageously be employed are selected from water, methanol, ethanol, n-propanol, isopropanol, n-hexane, ethylacetate, methylene chloride, chloroform, ethylene glycol monomethyl ether or mixtures thereof.

As stated above, the compounds of the invention are useful antibacterial agents. More exactly, they possess a remarkable in vitro activity both against Gram positive (as an example, various *Staph. aureus* strains) and Gram negative bacteria, some of them from clinical isolation, which can be found in the intestinal bacterial flora in pathologic conditions.

The results obtained with representative compounds of the invention are summarized in the following table. They represent the minimum concentration of active substance capable of inhibiting the growth in vitro of the pathogenic bacterium (M.I.C.) and are expressed as micrograms of substance per ml of culture medium ($\gamma$/ml).

TABLE 1 (M.C.I.)

| STRAIN | COMPOUND OF EXAMPLE | | | | | | | | | |
|---|---|---|---|---|---|---|---|---|---|---|
| | 1 | 2 | 3 | 5 | 6 | 7 | 8 | 10 | 11 | 12 |
| Staph. aureus 209 P FDA | <0.005 | <0.005 | <0.005 | <0.005 | <0.005 | <0.005 | <0.005 | <0.005 | <0.005 | <0.005 |
| Staph. aureus Colliva | <0.005 | <0.005 | <0.005 | <0.005 | <0.005 | <0.005 | <0.005 | <0.005 | <0.005 | <0.001 |
| Pseud. aeruginosa ATCC 10145 | n.d. | n.d. | n.d. | ~1.5 | n.d. | n.d. | n.d. | 0.7÷1.5 | 6÷12 | 3÷6 |
| Esch. coli Beltrami | 0.7 | 0.7 | 0.7-1.5 | ~12 | 0.7-1.5 | <0.7 | 0.7-1.5 | 6÷12 | 0.3 | 0.3÷0.7 |
| Esch. coli 47/9 | 12÷25 | ~12 | 12÷25 | ~12 | 12÷25 | 6÷12 | 12÷25 | ~12 | 6÷12 | 6÷12 |
| Esch. coli ML/35 | 6÷12 | 6÷12 | 12÷25 | ~25 | ~6 | 6÷12 | 6÷12 | 12÷25 | 3÷6 | 3÷6 |
| Kleb. pneumoniae Ottaviani | 12÷25 | 6÷12 | 12÷25 | ~12 | 12÷25 | 6÷12 | 12÷25 | 6÷12 | 3÷6 | 6÷12 |
| Proteus vulgaris ATCC 9484 | 12÷25 | ~6 | 12 | n.d. | ~12 | ~6 | 6÷12 | n.d. | 6÷12 | 6÷12 |
| Sal. p.tiphy B 0248 K Sclavo | 6÷12 | 12÷25 | 12 | 3÷6 | ~6 | 6÷12 | 6÷12 | ~3 | 3÷6 | 6÷12 |
| Salm. tiphymurium ATCC 13311 | ≅12 | 3÷6 | 3÷6 | 6÷12 | 6÷12 | 3÷6 | 3÷6 | 6÷12 | ~3 | ~3 |
| Salm. p.tiphy A | 12÷25 | ~6 | 12÷25 | n.d | 12÷25 | ~6 | 6÷12 | n.d. | ~3 | 3÷6 |
| Enter. cloacae ATCC13047 | n.d. | n.d. | n.d. | 6÷12 | n.d. | n.d. | 12÷25 | 6÷12 | 6÷12 | 6÷12 |
| Shigh. sonnei ATCC 9290 | 6÷12 | 12÷25 | 6÷12 | ~12 | 6÷12 | 12÷25 | 6÷12 | 6÷12 | ~1.5 | ~1.5 |
| Shigh. flexneri | ≅12 | ~12 | 3-6 | n.d. | 6÷12 | ~12 | 3-6 | n.d. | 3÷6 | 3÷6 |

< = less than
~ = about
n.d. = not determined

The compounds of the invention possess also a noteworthy in vivo activity against the experimental infection provoked by *Sthaphylococcus aureus* when administered by subcutaneous route. This in vivo activity, expressed as an $ED_{50}$ value, may vary between about 0.1 and about 0.5 mg/kg.

It has also been found that the compounds of the invention, unlike other rifamycin derivatives widely used in the therapy, are scarcely absorbed from animal organs and tissues when administered by oral route, and are found unaltered in the stool in a remarkable percentage with respect to the administered dosage. Thus, for instance, in a representative experiment carried out on groups of four rats fasted and normally feeded, which were orally given 100 mg/kg of the compound of Example 6, it was found that, after four hours from the administration only 0.2 μg/ml and 6.5 μg/g were absorbed respectively by the serum and the liver in the feeded rats, and only 0.1 μg/ml and 0.7 μg/g were absorbed respectively by the serum and the liver in the fasted rats.

In a further representative experiments aiming at evaluating the extent of the urinary and faecal elimination of the compounds of the invention, groups of six rats were orally given 25 mg/kg of the compound of Example 6. Stools and urine were collected for 72 hours, then the content of compound was determined by microbiological route.

After this period of time, almost 60% of the compound was found unaltered in the stools, whereas the amount of said compound in the urine could not be determined because of its very low concentration. These data, coupled with the remarkable in vitro activity of the compounds of the invention against Gram negative bacteria present in the intestinal bacterial flora in pathological situations indicate that the compound of formula I are useful as intestinal antibacterial agents. These properties were confirmed by experiments carried out on rats by determining the total number (total bacterial charge) in stool samples collected both from animals which received no compounds and from animals which daily received by oral route predetermined amounts of the compounds of the invention.

The experiments lasted seven days and were conducted on groups of six animals. The choice of the animal species (rat) is absolutely justified, as rats have an intestinal bacterial flora similar to that of humans.

The obtained results are reported in the following table, wherein the total bacterial charge is expressed as the decimal logarithm of the number of bacteria in one gram of collected fresh stools. As the representative compounds, those of Examples 6 and 11 were taken into consideration.

TABLE 2

| Compound of Example | Dose | | | | | |
|---|---|---|---|---|---|---|
| | 1 mg/kg/die per os total bacterial charge | | 10 mg/kg/die per os total bacterial charge | | 30 mg/kg/die per os total bacterial charge | |
| | aerobic | anaerobic | aerobic | anaerobic | aerobic | anaerobic |
| 6 | 4.50 | 6.00 | 4.50 | 3.60 | 4.50 | 3.30 |
| 11 | 3.50 | 4.83 | 5.00 | 2.83 | 8.20 | 3.75 |
| Controls | 6.00 | 9.83 | 5.40 | 7.33 | 9.67 | 6.50 |

The results reported in this table are self-explanatory. They clearly show that the compounds of the invention cause a marked reduction of the bacterial intestinal flora of the laboratory animals. It was also discovered that this action displayed by the compounds of the invention is even higher than that possessed by neomycin, an aminoglycoside antibiotic employed as intestinal antibacterial agent (see, for instance, Remington's Pharmaceutical Sciences, page 1126, 16th Edition, Mack Publishing Company, Pennsylvania, 1980) which, however, displays a lot of dangerous side effects (see again Remigton's Pharmaceutical Sciences, page 1274).

These favorable biological properties are coupled with a very low toxicity, being the $LD_{50}$ values per os both in rats and in mice always higher than 2000 mg/kg.

The use of the compounds of the invention as antibacterial agents refers to all industrially applicable acts and aspects of said use, including their incorporation into pharmaceutical compositions.

The pharmaceutical compositions containing the active ingredient are in fact a further specific object of the invention.

The compounds of the invention can therefore be administered by several routes, as an example by oral, topic or intramuscular route. For such administrations, the substances are embodied into conventional pharmaceutical dosage formulations. These formulations contain, in admixture with the active ingredient, the usual additives such as, for instance, sweetening, flavoring, coloring, coating and preservative agents, inert diluents such as, for instance, calcium or sodium carbonate, lactose and talc, binding agents, e.g. starch, gelatin and polyvinylpyrrolidone, suspending agents, e.g. methylcellulose or hydroxyethylcellulose, and wetting agents such as, for instance, lecithin, polyoxyethylene stearates and polyoxymethylene sorbitan monooleate. The preparation useful for the topical and intramuscular administration may contain the active ingredient dissolved or suspended in distilled and pyrogen-free water, in admixture with the commonly employed pharmaceutical carriers.

The invention can be better illustrated by means of the following examples which, however, must in no way be construed as a limitation of the scope of the invention itself.

The U.V. spectra have been recorded in absolute methanol with a Parkin-Elmer 552 spectrophotometer.

The I.R. spectra have been recorded in KBr with a Perkin-Elmer 281-B spectrophotometer.

The $^1$H-NMR and $^{13}$C-NMR, where not expressly specified, have been recorded in $CDCl_3$ with a Varian XL 100 spectrophotometer, using tetramethylsilane as the reference substance.

The reported data are in agreement with the proposed structures.

EXAMPLE 1

N-Dehydro-4-deoxy-2-imino-4'-methyl-pyrido[1',2':1,-2]imidazo[5,4-c]rifamycin S

A solution of 1.54 g (0.002 mole) of 3-bromo-rifamycin S dissolved in 10 ml of ethanol was added under stirring at room temperature with 0.430 g (0.004 mole) of 2-amino-4-methyl-pyridine. The reaction mixture was kept at this temperature for about two hours until complete disappearance of 3-bromo-rifamycin S [TLC-monitorage; eluting system $CHCl_3/CH_3OH=40/1$ (v/v)], then 250 ml of ethyl acetate were added. The organic phase was separated, washed first with 5% aqueous citric acid, then with water until pH 7 and subsequently dried over sodium sulfate. After evaporating to dryness, the obtained residue was taken up with ethanol from which the title compound separated. Yield: 1.35 g (86% of theoretical). M.p.: 228°–32° C. (with decomposition).

| U.V. Spectrum: | λmax (mμ) | $E^{1\%}_{1cm}$ |
|---|---|---|
| | 242 | 544 |

-continued

| U.V. Spectrum: | λmax (mμ) | $E_{1cm}^{1\%}$ |
|---|---|---|
| | 272 | 391 |
| | 320 | 204 |
| | 342 | 190 |
| | 375 | 76 |
| | 415 | 116 |

I.R. Spectrum: characteristic absorption bands were observed at the following frequencies (in cm$^{-1}$): 3440 (b), 2960 (s), 2920 (w), 2860 (w), 2800 (w), 1728 (s), 1708 (s), 1635 (w), 1590 (s), 1500 (w).

b=broad; s=strong; w=weak.

$^1$H-NMR Spectrum: characteristic resonance peaks were observed at the following δ (expressed as p.p.m.): 0.02 (d, 3H); 0.04 (d, 3H); 0.53 (d, 3H); 0.91 (d, 3H); 1.77 (s, 3H); 2.06 (s, 3H); 2.25 (s, 3H); 2.28 (s, 3H); 2.54 (s, 3H); 2.75-3.05 (m, 2H); 3.10 (s, 3H); 3.45 (s, 1H); 3.58 (d, 1H); 4.02 (d, 1H); 4.82 (d, 1H); 5.36 (dd, 1H); 6.32 (dd, 1H); 6.5-6.8 (m, 3H); 7.00 (dd, 1H); 7.80 (s, 1H); 9.32 (d, 1H); 13.4 (s, 1H).

s=singlet; d=doublet; m=multiplet; dd=doublet of doublet $^{13}$C-NMR Spectrum: characteristic resonance peaks were observed at the following δ (expressed as p.p.m.): 7.35; 8.18; 9.55; 10.61; 14.18; 20.69; 21.44; 21.80; 22.26; 34.23; 36.45; 37.05; 39.80; 57.30; 73.98; 76.18; 77.06; 78.47; 108.20; 109.82; 110.45; 111.22; 117.63; 118.31; 118.89; 120.90; 125.13; 127.09; 128.44; 132.83; 138.61; 139.71; 142.03; 142.44; 146.45; 146.52; 150.01; 170.98; 172.57; 180.62; 181.92.

EXAMPLES 2-5

The following compounds were prepared substantially according to the same procedure of the above Examples, starting from an appropriate 3-halo-rifamycin S of formula II and a predetermined compound of formula III.

EXAMPLE 2

N-Dehydro-4-deoxy-2-imino-5'-methyl-pyrido[1',2':1,-2]imidazo[5,4-c]rifamycin S, from 1.54 g (0.002 moli) of 3-bromo-rifamycina S and 0.432 g (0.004 moli) of 2-amino-3-methyl-pyridine. Yield: 1.2 g. (78% of theoretical).
M.p.: 208°-12° C. (with decomposition).

| U.V. Spectrum | λmax (mμ) | $E_{1cm}^{1\%}$ |
|---|---|---|
| | 238 | 574 |
| | 270 | 370 |
| | 310 | 298 |
| | 370 | 103 |
| | 422 | 131 |
| | 440 | 122 |

I.R. Spectrum: characteristic absorption bands were observed at the following frequencies (in cm$^{-1}$): 3450 (b), 2980 (s), 2920 (s), 2870 (s), 2820 (s), 1735 (s), 1710 (s), 1660 (s), 1630 (s), 1600 (s), 1555 (s).

b=broad; s=strong.

$^1$H-NMR Spectrum: characteristic resonance peaks were observed at the following δ (expressed as p.p.m.): 0.0 (d, 3H) 0.54 (d, 3H); 0.88 (d, 3H); 1.3 (d, 3H); 1.73 (s, 3H); 2.02 (s, 3H); 2.23 (s, 3H); 2.27 (s, 3H); 2.4 (s, 3H); 2.5-3.0 (m, 2H); 3.05 (s, 3H); 3.42 (s, 1H); 3.52 (d, 1H); 3.9 (d, 1H); 4.74 (d, 1H); 5.3 (q, 1H); 6.3 (d, 1H); 6.4-7.0 (m, 3H); 7.35 (d, 1H); 7.58 (d, 1H); 9.22 (s, 1H); 13.25 (s, 1H).

s=singlet; d=doublet; q=quartet; m=multiplet

EXAMPLE 3

N-Dehydro-4-deoxy-2-imino-3'-methyl-pyrido[1',2':1,-2]imidazo[5,4-c]rifamycin S, from 1.54 g (0.002 mole) of 3-bromo-rifamycin S e 0.432 g (0.004 mole) of 2-amino-5-methyl-pyridine. Yield: 1.05 g (67% of theoretical).

| U.V. Spectrum: | λmax (mμ) | $E_{1cm}^{1\%}$ |
|---|---|---|
| | 242 | 459 |
| | 274 | 362 |
| | 322 | 260 |
| | 345 | 155 |
| | 384 | 79 |
| | 418 | 99 |
| | 510 | 36 |

I.R. Spectrum: characteristic absorption bands were observed at the following frequencies (in cm$^{-1}$): 3410 (b), 3340 (b), 2960 (s), 2920 (s), 2880 (w), 2840 (w), 1735 (s), 1710 (w), 1655 (s), 1620 (vw), 1598 (s), 1505 (s)

s=strong b=broad w=weak vw=very weak $^1$H-NMR Spectrum: characteristic resonance peaks were observed at the following δ (expressed as p.p.m.): 0.04 (d, 3H); 0.55 (d, 3H); 0.93 (d, 3H); 1.1-1.5 (m, 4H); 1.8 (s, 3H); 2.09 (s, 3H); 2.25 (s, 3H); 2.32 (s, 3H); 2.48 (s, 3H); 2.7-3.3 (m, 2H); 3.13 (s, 3H); 3.52 (s, 1H); 3.62 (d, 1H); 4.1 (d, 1H); 4.9 (d, 1H); 5.45 (q, 1H); 6.48 (d, 1H); 6.6-6.9 (m, 3H); 7.55 (d, 1H); 8.08 (d, 1H); 9.55 (s, 1H); 13.35 (s, 1H).

s=singlet; d=doublet; m=multiplet; q=quartet.

EXAMPLE 4

5'-Benzyloxy-N-dehydro-4-deoxy-2-imino-pyrido[1',2':1,2]imidazo[5,4-c]rifamycin S, from 1.54 g (0.002 mole) of 3-bromo-rifamycin S and 1.6 g (0.008 mole) of 2-amino-3-benzyloxy-pyridine. Yield: 0.840 g (46% of theoretical). M.p. 198°-203° C. (with decomposition).

| U.V. Spectrum: | λmax (mμ) | $E_{1cm}^{1\%}$ |
|---|---|---|
| | 245 | 536 |
| | 275 | 349 |
| | 320 | 238 |
| | 420 | 95 |

I.R. Spectrum: characteristic absorption bands were observed at the following frequencies (in cm$^{-1}$): 3450 (b), 2980 (w), 2970 (s), 2930 (s), 2920 (vw), 1730 (s), 1710 (s), 1655 (s), 1625 (vw), 1595 (s), 1545 (s), 1505 (s).

b=broad; s=strong; w=weak; vw=very weak $^1$H-NMR Spectrum: characteristic resonance peaks observed at the following δ (expressed as p.p.m.): 0.08 (d, 3H); 0.53 (d, 3H); 0.94 (d, 3H); 1.1-1.6 (m, 4H); 1.82 (s, 3H); 1.12 (s, 3H); 1.3 (s, 3H); 1.34 (s, 3H); 2.7-3.2 (m, 2H); 3.15 (s, 3H); 3.3-3.8 (m, 2H); 4.10 (d, 1H); 4.88 (d, 1H); 5.42 (q, 1H); 5.9 (s, 2H); 6.42 (d, 1H); 6.5-6.8 (m, 3H); 6.9-7.2 (m, 2H); 7.3-7.8 (m, 5H); 9.14 (q, 1H); 13.39 (s, 1H).

s=singlet; d=doublet; m=multiplet; q=quartet

EXAMPLE 5

N-Dehydro-4-deoxy-2-imino-isoquinolino[2',1':1,-2]imidazo[5,4-c]rifamycin S, from 0.820 g (0.001 mole) of 3-iodo-rifamycin S and 0.288 g (0.002 mole) of 1-amino-isoquinoline. Yield: 0.510 g (62% of theoretical). M.p.: 198°-203° C. (with decomposition).

| U.V. Spectrum: | λmax (mμ) | $E_{1cm}^{1\%}$ |
|---|---|---|
| | 256 | 765 |
| | 322 | 264 |
| | 338 | 260 |
| | 413 | 107 |

I.R. Spectrum: characteristic absorption bands were observed at the following frequencies (in cm$^{-1}$): 3460; 3120 (w); 3060 (w), 2980 (s); 2930 (s); 2880; 2820; 1735 (s); 1715 (s); 1660; 1625 (vw); 1600; 1525.

s=strong; w=weak; vw=very weak $^1$H-NMR Spectrum: characteristic resonance peaks were observed at the following δ (expressed as p.p.m.): 0.06 (d, 3H); 0.22 (d, 3H); 0.5 (d, 3H); 0.83 (d, 3H); 1.79 (s, 3H); 2.00 (s, 3H); 2.26 (s, 3H); 2.3 (s, 3H); 2.5-3.00 (m, 2H), 3.10 (s, 3H); 3.45 (s, 1H); 3.6 (d, 1H); 4.00 (s, 1H); 4.76 (d, 1H); 5.39 (q, 1H); 6.8 (m, 4H); 7.38 (d, 1H); 7.6-7.9 (m, 3H); 9.00 (m, 1H); 9.20 (d, 1H).

s=singlet; d=doublet; q=quartet; m=multiplet.

EXAMPLE 6

4-Deoxy-4'-methyl-pyrido[1',2':1,2]imidazo[5,4-c]rifamycin SV

1 Gram (0.00127 mole) of the compound of Example 1 was dissolved in 50 ml of absolute ethanol and the resulting solution was added with 20 ml of a 5% aqueous solution of L(−)-ascorbic acid. The mixture was kept at room temperature for about 1 hour until disappearance of the compound of Example 1 [TLC-monitorage; eluting system CHCl$_3$/CH$_3$OH=23/2 (v/v)], then it was extracted with 50 ml of ethyl acetate. After washing with water to pH 7 and drying over sodium sulfate, the solvent was evaporated off and the obtained residue was taken up with a 70/30 (v/v) mixture of glycol monomethyl ether/water. The title compound separated, which was recovered by filtration: Yield: 0.840 g (85% of theoretical). M.p.: 200°-5° C. (with decomposition).

| U.V. Spectrum: | λmax (mμ) | $E_{1cm}^{1\%}$ |
|---|---|---|
| | 232 | 489 |
| | 260 | 339 |
| | 292 | 295 |
| | 320 | 216 |
| | 370 | 119 |
| | 450 | 159 |

I.R. Spectrum: characteristic absorption bands were observed at the following frequencies (in cm$^{-1}$): 3440 (b), 2960 (s), 2920 (s), 2860 (w), 2820 (vw), 1705 (s), 1640 (s), 1580 (s), 1500 (s)

b=broad; s=strong; w=weak; vw=very weak $^1$H-NMR Spectrum: characteristic resonance peaks were observed at the following δ (expressed as p.p.m.): −0.56 (d, 3H); 0.14 (d, 3H); 0.74 (d, 3H); 0.94 (d, 3H); 1.94 (s, 3H); 1.98 (s, 3H); 2.02 (s, 3H); 2.26 (s, 3H); 2.63 (s, 3H); 3.00 (s, 3H); 3.2-3.9 (m, 3H); 4.15-5.20 (m, 2H); 5.9-6.9 (m, 4H); 7.06 (dd, 1H); 7.38 (s, 1H); 8.39 (s, 1H); 8.43 (d, 1H); 11.0 (s, 1H); 13.12 (s, 1H).

s=singlet; d=doublet; m=multiplet; dd=doublet of doublet.

$^{13}$C-NMR Spectrum: characteristic resonance peaks were observed at the following (expressed as p.p.m.): 6.98; 8.06; 8.21; 10.76; 17.56; 20.43; 20.78; 21.44; 22.35; 32.91; 36.93; 37.78; 38.59; 56.99; 72.65; 73.91; 76.75; 77.86; 97.83; 103.86; 104.09; 108.97; 109.99; 112.03; 114.96; 115.52; 117.61; 119.26; 122.99; 125.35; 128.44; 128.96; 136.21; 138.87; 141.75; 142.10; 147.74; 155.10; 170.63; 171.89; 182.19; 188.84.

EXAMPLES 7-10

The following compounds were prepared substantially as described in Example 6.

EXAMPLE 7

4-Deoxy-5'-methyl-pyrido [1',2':1,2] imidazo [5,4-c] rifamycin SV, from 1 g (0.00127 mole) of the compound of Example 2. Yield: 0.940 g (95% of theoretical). M.p.: 185°-90° C. (with decomposition).

| U.V. Spectrum: | λmax (mμ) | $E_{1cm}^{1\%}$ |
|---|---|---|
| | 217 | 470 |
| | 235 | 544 |
| | 262 | 333 |
| | 273 | 303 |
| | 292 | 295 |
| | 320 | 205 |
| | 356 | 99 |
| | 373 | 122 |
| | 440 | 164 |
| | 454 | 166 |

I.R. Spectrum: characteristic absorption bands were observed at the following frequencies (in cm$^{-1}$): 3440 (b), 3300 (b), 3200 (b), 2960 (s), 2920 (w), 2850 (vw), 1730 (s), 1710 (w), 1640 (s), 1595 (s), 1580 (b), 1555 (w)

b=broad; s=strong; w=weak; vw=very weak $^1$H-NMR Spectrum: characteristic resonance peaks were observed at the following δ(expressed as p.p.m.):- 0.64 (d, 3H); 0.02 (d, 3H); 0.45 (d, 3H); 0.90 (d, 3H); 1.75 (s, 3H); 1.94 (s, 3H); 1.97 (s, 3H); 2.23 (s, 3H); 2.45 (s, 3H); 2.95 (s, 3H); 2.6-5.8 (m, 5H); 4.5-5.25 (m, 2H); 5.5-7.0 (m, 4H); 7.25-7.75 (m, 2H); 8.27 (s, 1H); 8.47 (s, 1H); 14.86 (s, 1H); 16.77 (s, 1H)

s=singlet; d=doublet; m=multiplet

EXAMPLE 8

4-Deoxy-3'-methyl-pyrido [1',2':1,2] imidazo [5,4-c] rifamycin SV, from 1.5 g (0.00191 mole) of the compound of Example 3. Yield: 1.46 g (96.3% of theoretical). M.p. 193°-98° C. (with decomposition).

| U.V. Spectrum: | λmax (mμ) | $E_{1cm}^{1\%}$ |
|---|---|---|
| | 218 | 493 |
| | 244 | 433 |
| | 258 | 338 |
| | 274 | 301 |
| | 294 | 315 |
| | 304 | 207 |
| | 360 | 104 |
| | 373 | 123 |
| | 448 | 166 |

I.R. Spectrum: characteristic absorption bands were observed at the following frequencies (in cm$^{-1}$): 3340 (b), 3300 (b), 2960 (s), 2925 (s), 2870 (vw), 2850 (s), 1730 (s), 1710 (vw), 1650 (vw), 1640 (s), 1600 (vw), 1585 (s), 1565 (w), 1525 (wv), 1505 (s)

b=broad; s=strong; w=weak; vw=very weak $^1$H-NMR Spectrum: characteristic resonance peaks were observed at the following δ(expressed as p.p.m.): -0.7 (d, 3H); 0.05 (d, 3H); 0.68 (d, 3H); 0.87 (d, 3H); 1.73

(s, 3H); 1.92 (s, 3H); 1.97 (s, 3H); 2.23 (s, 3H); 2.63 (s, 3H); 2.92 (s, 3H); 3.25-4.00 (m, 5H); 4.6-5.10 (m, 2H); 5.9-6.8 (m, 4H); 7.13 (q, 1H); 7.6 (q, 1H); 8.48 (q, 1H); 14,14 (s, 1H); 16.65 (s, 1H)

s=singlet; d=doublet; m=multiplet; q=quartet

EXAMPLE 9

5'-Benzyloxy-4-deoxy-pyrido [1',2':1,2] imidazo [5,4-c] rifamycin SV, from 1.5 g (0.00167 mole) of the compound of Example 4. Yield: 1.6 g (96.4% of theoretical). M.p. 175°-80° C. (with decomposition).

| U.V. Spectrum: | λmax (mμ) | $E^{1\%}_{1cm}$ |
|---|---|---|
| | 238 | 561 |
| | 260 | 339 |
| | 282 | 311 |
| | 324 | 194 |
| | 355 | 100 |
| | 370 | 129 |
| | 432 | 153 |
| | 452 | 167 |

I.R. Spectrum: characteristic absorption bands were observed at the following frequencies (in cm$^{-1}$): 3520 (w), 3410 (w), 3310 (w), 3210 (w), 3140 (w), 3060 (vw), 2960 (s), 2920 (s), 1750 (vw), 1730 (vw), 1710 (w), 1650 (s), 1600 (w), 1575 (s), 1505 (s)

s=strong; w=weak; vw=very weak $^1$H-NMR Spectrum: characteristic resonance peaks were observed at the following δ(expressed as p.p.m.; the spectrum was recorded in CDCl$_3$+CD$_3$OD): -0.65 (d, 3H); -0.25 (d, 3H); 0.73 (d, 3H); 0.90 (d, 3H); 1.92 (s, 3H); 1.97 (s, 3H); 2.02 (s, 3H); 2,28 (s, 3H); 2.83 (d, 1H); 2.97 (s, 3H); 3.1-4.0 (m, 1H); 4.5-5.2 (m, 2H); 5.4 (s, 2H); 5.8-6.95 (m, 4H); 7.0-7.75 (m, 7H); 8.21 (d. 1H)

s=singlet; d=doublet; m=multiplet

EXAMPLE 10

4-Deoxy-isoquinolino [2',1':1,2] imidazo [5,4-c] rifamycin SV, from 0.410 g (0.0005 mole) of the compound of Example 5. Yield: 0.400 g (97.5% of theoretical). M.P.: 181°-86° C. (with decomposition)

| U.V. Spectrum: | λmax (mμ) | $E^{1\%}_{1cm}$ |
|---|---|---|
| | 253 | 532 |
| | 288 | 363 |
| | 300 | 346 |
| | 320 | 290 |
| | 382 | 120 |
| | 430 | 120 |

I.R. Spectrum: characteristic absorption bands were observed at the following frequencies (in cm$^{-1}$): 3440 (b), 3140 (b), 2910 (s), 2850 (w), 1700 (s), 1630 (b), 1610 (b), 1580 (w), 1555 (vw), 1535 (vw).

b=broad; s=strong; w=weak; vw=very weak $^1$H-NMR Spectrum: characteristic resonance peaks were observed at the following δ(expressed as p.p.m.): -0.65 (d, 3H); 0.04 (d, 3H); 0.7 (d, 3H); 0.88 (d, 3H); 1.55 (s, 3H); 1.92 (s, 3H); 2.02 (s, 3H); 2.27 (s, 3H); 2.77 (d, 1H); 2.94 (s, 3H); 3.00-3.90 (m, 4H); 4.78 (d, 1H); 4.93 (q, 1H); 5.75-7.00 (m, 4H); 7.34 (d, 1H); 7.6-8.0 (m, 6H); 16.6 (m, 1H).

s=singlet; d=doublet; m=multiplet; q=quartet

EXAMPLE 11

4-Deoxy-pyrido [1',2':1,2] imidazo [5,4-c] rifamycin SV

A solution of 2.32 g (0.003 mole) of 3-bromo-rifamycin S in 50 ml of ethanol was added at room temperature under stirring with 1.41 g (0.015 mole) of 2-amino-pyridine. The resulting mixture was kept at the same temperature for 4 hours until complete disappearance of 3-bromo-rifamycin S (TLC-monitorage, eluting system: ethyl acetate), then it was added with 300 ml of ethyl acetate. After washing the organic phase with a 5% aqueous solution of citric acid and, subsequently, with water to pH 7, and drying over sodium sulfate, the solvent was evaporated off, the obatined residue was dissolved in some ethanol and the resulting solution was added with 20 ml of a 5% aqueous solution of L(—) ascorbic acid. The reaction mixture was kept at room temperature for 15 minutes, added with 50 ml of CHCl$_3$, and subsequently washed with water to pH 7. After drying over sodium sulfate and evaporating off the solvent, the obtained residue was taken up with ethyl acetate. The title product separated, which was recovered by filtration.

Yield: 1.8 g (77.7% of theoretical). M.p.: 170°-75° C. (with decomposition).

| U.V. Spectrum: | λmax (mμ) | $E^{1\%}_{1cm}$ |
|---|---|---|
| | 234 | 521 |
| | 258 | 329 |
| | 293 | 301 |
| | 373 | 122 |
| | 450 | 160 |

I.R. Spectrum: characteristic absorption bands were observed at the following frequencies (in cm$^{-1}$): 3440 (b), 3300 (b), 3200 (b), 2970 (s), 2930 (s), 2880 (w), 2820 (w), 1635 (s), 1605 (w), 1585 (w), 1575 (w), 1605 (s).

b=broad; s=strong; w=weak $^1$H-NMR Spectrum: characteristic resonance peaks were observed at the following δ(expressed a p.p.m.): -0.54 (d, 3H); 0.18 (d, 3H); 0.76 (d, 3H); 0.96 (d, 3H); 1.92 (s, 3H); 1.96 (s, 3H); 1.98 (s, 3H); 2.27 (s, 3H); 2.88 (d, 1H); 3.00 (s, 3H); 3.34 (d, 1H); 3.66 (d, 1H); 4.92 (d, 1H); 5.06 (m, 1H); 5.5-5.9 (m, 3H); 6.6-7.0 (m, 1H); 7.1-7.4 (m, 1H); 7.6-8.0 (m, 2H); 8.39 (s, 1H); 8.66 (d, 1H); 13.8 (s, 1H); 15.4 (s, 1H).

s=singlet; d=doublet; m=multiplet.

$^{13}$C-NMR Spectrum: characteristic resonance peaks were observed at the following δ(expressed as p.p.m.): 6.98; 8.37; 10.84; 17.53; 20.41; 20.79; 21.29; 32.96; 36.93; 37.86; 38.56; 57.08; 72.82; 74.00; 76.88; 77.87; 97.93; 104.23; 104.35; 108.94; 111.49; 112.28; 114.96; 115.02; 115.31; 119.69; 123.33; 125.42; 128.31; 129.77; 134.31; 137.06; 138.54; 141.97; 142.27; 155.14; 170.61; 171.86; 171.98; 182.32; 188.79.

EXAMPLE 12

N-Dehydro-4-deoxy-pyrido [1',2':1,2] imidazo [5,4-c] rifamycin S

1 Gram of manganese dioxide was added to a solution of 1.5 g (0.00194 mole) of the compound of Example 11 in 30 ml of CHCl$_3$. The reaction mixture was kept at room temperature until disappearance of the starting compound (TLC-monitorage; eluting system: ethyl acetate). The oxidizer was then removed by filtration, the precipitate was washed with methanol, the methanolic and chloroform phases were joined together and washed with a 5% aqueous solution of citric acid and then with water to neutrality. After drying over sodium sulfate, the solvent was evaporated off and a residue was obtained which was taken up with chloroform and n-hexane. The title compound separated, which was recovered by filtration. Yield: 1.45 g (97% of theoretical). M.p. 207°-12° C. (with decomposition).

| U.V. Spectrum: | λmax (mμ) | $E_{1cm}^{1\%}$ |
|---|---|---|
| | 233 | 429 |
| | 272 | 381 |
| | 315 | 255 |
| | 342 | 175 |
| | 410 | 116 |

I.R. Spectrum: characteristic absorption bands were observed at the following frequencies (in cm$^{-1}$): 3460 (b), 3340 (b), 2960 (s), 2930 (s), 2880 (w), 2850 (w), 1735 (s), 1710 (vw), 1655 (s), 1625 (w), 1600 (s), 1505 (s).

b=broad; s=strong; w=weak; vw=very weak $^1$H-NMR Spectrum: characteristic resonance peaks were observed at the following δ(expressed as p.p.m.): 0.02 (d, 3H); 0.5 (d, 3H); 0.9 (d, 3H); 1.77 (s, 3H); 2.04 (s, 3H); 2,26 (s, 3H); 2.29 (s, 3H); 2.75-3.05 (m, 2H); 3.10 (s, 3H); 3.42 (s, 1H); 3.58 (d, 1H); 4.01 (d, 1H); 4.82 (d, 1H); 5.37 (q, 1H); 6.34 (dd, 1H); 6.45-6.8 (m, 3H); 7.18 (m, 1H); 7.58 (m, 1H); 8.04 (d, 1H); 9.50 (d, 1H); 13.28 (s, 1H).

s=singlet; d=doublet; dd=doublet of doublet; m=multiplet; q=quartet $^{13}$C-NMR Spectrum: characteristic resonance peaks were observed at the following δ(expressed in p.p.m.): 7.36; 8.22; 9.58; 10.71; 14.14; 20.70; 21.43; 22.25; 34.24; 36.45; 37.01; 39.75; 57.31; 73.94; 76.2; 76.91; 78.38; 108.19; 109.99; 110.36; 111.40; 116.52; 117.79; 119.55; 120.75; 125.01; 128.01; 128.32; 130.09; 132.67; 138.67; 139.99; 142.40; 146.31; 146.64; 149.48; 171.22; 172.46; 172.60; 180.26; 181.82; 192.98.

EXAMPLE 13

25-Desacetyl-4-deoxy-4'-merthyl-pyrido [1',2':1,2] imidazo [5,4-c] rifamycin SV

A solution of 1.57 g (0.002 mole) of the compound of Example 6 and 0.240 g of NaOH in 60 ml of methanol was kept at room temperature for about three hours, until disappearance of the starting compound [TLC-monitorage; eluting system: CHCl$_3$/CH$_3$OH=23/2 (v/v)]. The reaction mixture was then extracted with 300 ml of CHCl$_3$ and the organic extract was first washed with a 10% aqueous solution of citric acid and then with water to neutrality. After drying over sodium sulfate and removing the solvent by evaporation, the obtained residue was taken up with ethyl acetate. The title compound separated, which was recovered by filtration. Yield: 1.07 g (72% of theoretical). M.p. 199°-200° C. (with decomposition).

| U.V. Spectrum: | λmax (mμ) | $E_{1cm}^{1\%}$ |
|---|---|---|
| | 234 | 465 |
| | 260 | 305 |
| | 232 | 274 |
| | 310 | 232 |
| | 372 | 93 |
| | 436 | 138 |

I.R. Spectrum: characteristic absorption bands were observed at the following frequencies (in cm$^{-1}$): 3420 (b), 3330 (b), 2960 (s), 2920 (s), 2850 (s), 1735 (vw), 1725 (s), 1655 (w), 1650 (w), 1630 (vw), 1595 (s), 1585 (vw), 1505 (w).

b=broad; s=strong; w;32 weak; vw=very weak $^1$H-NMR Spectrum: characteristic resonance peaks, recorded in CDCl$_3$+CD$_3$OD, were observed at the following δ(expressed as p.p.m.): -0.68 (d, 3H); -0.20 (d, 3H); 0.74 (d, 3H); 0.92 (d, 3H); 1.88 (s, 3H); 2.03 (s, 3H); 2.20 (s, 3H); 2.58 (s, 3H); 3.05 (s, 3H); 2.75-3.95 (m, 4H); 4.75-5.14 (m, 1H); 6.00-6.5 (m, 4H); 7.05 (d, 1H); 7.48 (d, 1H); 8.40 (d, 1H).

s=singlet; d=doublet; m=multiplet

EXAMPLE 14

25-Desacetyl-N-dehydro-4-deoxy-2-imino-4'-methyl-pyrido [1',2':1,2] imidazo [5,4-c] rifamycin S This compound was prepared substantially as described in Example 12, starting from 0.740 g (0.001 mole) of the compound of Example 13. Yield: 0.720 g (97% of theoretical). M.p.: 200°-5° C. (with decomposition).

| U.V. Spectrum: | λmax (mμ) | $E_{1cm}^{1\%}$ |
|---|---|---|
| | 234 | 465 |
| | 260 | 305 |
| | 292 | 274 |
| | 310 | 232 |
| | 372 | 93 |
| | 436 | 138 |

I.R. Spectrum: characteristic absorption bands were observed at the following frequencies (in cm$^{-1}$): 3400 (b), 2960 (s), 2920 (s), 2870 (s), 1725 (s), 1655 (w), 1645 (w), 1630 (vw), 1595 (s), 1585 (vw), 1505 (s)

b=broad; s=strong; w=weak; vw=very weak;

$^1$H-NMR Spectrum: characteristic resonance peaks werre observed at the following δ(expressed as p.p.m.): 0.25 (d, 3H); 0.42 (d, 3H); 0.65 (d, 3H); 0.90 (d, 3H); 1.76 (s, 3H); 2.20 (s, 6H); 2.48 (s, 3H); 3.15 (s, 3H); 2.8-4.1 (m, 7H); 5.24 (q, 1H); 5.8-6.75 (m, 4H); 6.94 (d, 1H); 7.12 (d, 1H); 9.25 (d, 1H); 13.25 (s, 1H).

s=singlet; d=doublet; m=multiplet; q=quartet

By operating substantially according to the procedure illustrated in the above examples, the following compounds falling within the scope of the general formula I can be prepared.

| A | -x- | R | R$_1$ | R$_2$ | R$_3$ |
|---|---|---|---|---|---|
| A$_1$ | nil | CH$_3$CO | H | -4'-CH$_2$—CH$_2$—OH | H |
| A$_1$ | nil | CH$_3$CO | H | -4'-CH$_2$—CH$_2$—CH$_2$OH | H |
| A$_1$ | nil | CH$_3$CO | H | -4'-CH$_2$—CH$_2$—N(CH$_3$)$_2$ | H |
| A$_1$ | nil | CH$_3$CO | H | -4'-CH$_2$—N(CH$_3$)$_2$ | H |
| A$_1$ | nil | CH$_3$CO | H | -4'CH$_2$—CH$_2$—CH$_2$—N(CH$_3$)$_2$ | H |
| A$_1$ | nil | CH$_3$CO | -3'-CH$_3$ | -4'CH$_2$—CH$_2$—CH$_2$—N(CH$_3$)$_2$ | H |
| A$_1$ | nil | CH$_3$CO | -4'-C$_2$H$_5$ | -5'-CH$_2$—CH$_2$—CH$_2$—OH | H |
| A$_1$ | nil | CH$_3$CO | -5'-CH$_3$ | -3'-CH$_2$—CH$_2$—N(CH$_3$)$_2$ | H |
| A$_1$ | nil | H | H | -5'-CH$_2$CH$_2$—N(CH$_3$)$_2$ | H |
| A$_1$ | nil | H | -4'-CH$_3$ | -3'-CH$_2$CH$_2$—N(CH$_3$)$_2$ | H |
| A$_2$ | bond | CH$_3$CO | H | -4'-CH$_2$—CH$_2$—N(CH$_3$)$_2$ | nil |
| A$_2$ | bond | CH$_3$CO | H | -4'CH$_2$—CH$_2$—CH$_2$—N(CH$_3$)$_2$ | nil |
| A$_1$ | nil | CH$_3$CO | H | -4'-NO$_2$ | H |
| A$_2$ | bond | CH$_3$CO | H | -4'-NO$_2$ | nil |

The compounds of formula II were prepared according to the method described in U.S. Pat. No. 4,179,438. The substances of formula III are commercial products.

We claim:

1. A compound of formula

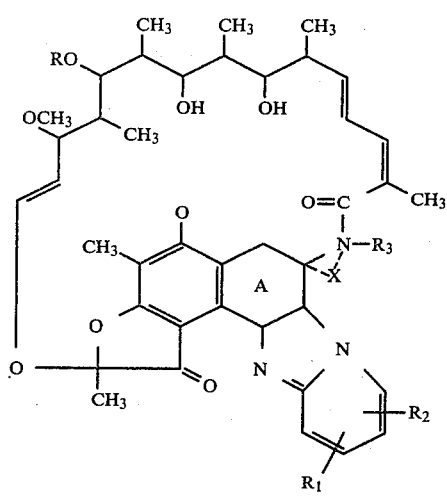

wherein:
A is

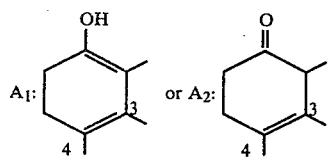

—x— is a covalent chemical bond or nil;
R is hydrogen or acetyl;
$R_1$ and $R_2$ independently represent hydrogen, ($C_{1-4}$) alkyl, benzyloxy, mono- and di-($C_{1-3}$) alkylamino-($C_{1-4}$) alkyl, ($C_{1-3}$)alkoxy- ($C_{1-4}$)alkyl, hydroxymethyl, hydroxy-($C_{2-4}$)-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, —x— is nil and $R_3$ is a hydrogen atom; with the further proviso that, when A is $A_2$, —x— is a covalent chemical bond and $R_3$ is nil.

2. A compound as defined in claim 1, wherein A is $A_1$ or $A_2$ as above indicated, —x— is a covalent chemical bond or nil, R is hydrogen or acetyl, $R_1$ and $R_2$ independently represent hydrogen, ($C_{1-4}$)alkyl, benzyloxy, hydroxy-($C_{2-4}$) alkyl, di-($C_{1-3}$) alkylamino-($C_{1-4}$) alkyl, nitro or $R_1$ and $R_2$ taken together with two consecutive carbon atoms of the pyridine nucleus form a benzene ring and $R_3$ is a hydrogen atom or nil; with the proviso that, when A is $A_1$, —x— is nil and $R_3$ is a hydrogen atom; with the further proviso that, when A is $A_2$, —x— is a covalent chemical bond and $R_3$ is nil.

3. A compound as defined in claim 1, wherein A is $A_1$ or $A_2$ as above indicated, —x— is a covalent chemical bond or nil, R is acetyl, $R_1$ and $R_2$ independently represent hydrogen, ($C_{1-4}$) alkyl or $R_1$ and $R_2$ taken together with two consecutive carbon atoms of the pyridine nucleus form a benzene ring and $R_3$ is a hydrogen atom or nil; with the proviso that, when A is $A_1$, —x— is nil and $R_3$ is a hydrogen atom; with the further proviso that, when A is $A_2$, —x— is a covalent chemical bond and $R_3$ is nil.

4. A compound as defined in claim 1, which is 4-deoxy-4'-methyl-pyrido[1',2'-1,2]imidazo [5,4-c]rifamycin SV.

5. A compound as defined in claim 1, which is 4-deoxy-pyrido [1',2':1,2]imidazo [5,4-c] rifamycin SV.

6. A process for preparing a compound of formula

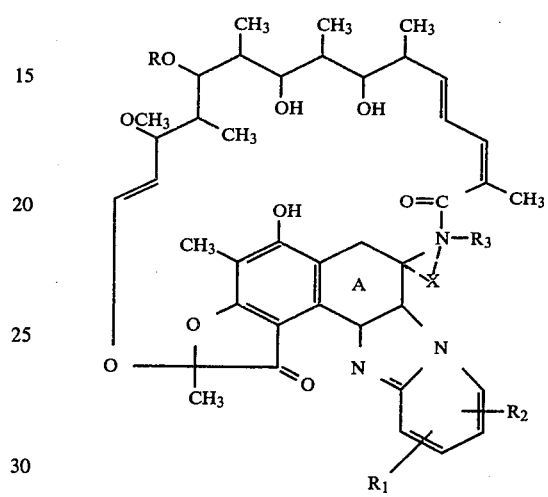

wherein:
A is

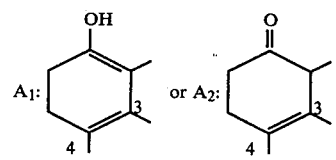

—x— is a covalent chemical bond or nil;
R is hydrogen or acetyl;
$R_1$ and $R_2$ independently represent hydrogen, ($C_{1-4}$) alkyl, benzyloxy, mono- and di-($C_{1-3}$)alkylamino($C_{1-4}$)alkyl, ($C_{1-3}$)alkoxy- ($C_{1-4}$)alkyl, hydroxymethyl, hydroxy-($C_{2-4}$)-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, —x— is nil and $R_3$ is a hydrogen atom; with the further proviso that, when A is $A_2$, —x— is a covalent chemical bond and $R_3$ is nil, which consists of reacting a molar amount of a 3-halorifamycin S of formula:

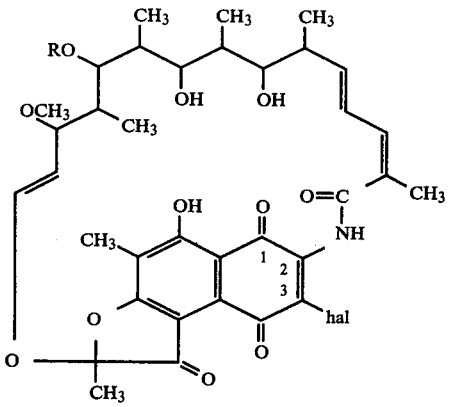

wherein hal stands for a halogen atom and R is hydrogen or acetyl, with a molar excess of a compound of formula

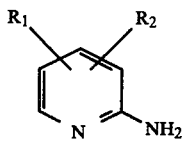

where $R_1$ and $R_2$ are as above defined, in the presence of an inert organic solvent, at room temperature, for a period of time comprised between about 1 and about 4 hours, whereby a compound of formula 1 is obtained in which A is $A_2$, R, $R_1$, and $R_2$ are as above defined, —x— is a covalent chemical bond and $R_3$ is nil, which can be transformed into the corresponding compounds of formula 1 wherein A is $A_1$, R, $R_1$ and $R_2$ are as above defined, —x— is nil and $R_3$ stands for a hydrogen atom, by treatment with a suitable reducing agent, in an inert organic solvent; said process being further characterized in that:

(a) the compound of formula 1 wherein A identifies the structure $A_1$, R, $R_1$ and $R_2$ are as above defined, —x— is nil and $R_3$ stands for a hydrogen atom, is transformed into the corresponding compounds of formula 1 wherein A is $A_2$, R, $R_1$ and $R_2$ are as above defined, —x— is a covalent chemical bond and $R_3$ represents nil, by treatment with a suitable oxidizing agent selected from manganese dioxide, lead tetracetate, dichloro-dicuano-benzoquinone, 2,3,4,5-tetrachloro-benzoquinone, 2,3,5,6-tetrachloro-benzoquinone and analogs;

(b) the compound of formula 1 wherein R is acetyl and is converted into the corresponding compound of formula 1 wherein R is hydrogen, by mild alkaline hydrolysis.

7. A process as defined in claim 6, wherein from about 1 to about 8 molar equivalents of the compound of formula III are used for each molar equivalent of the rifamycin derivative of formula II.

8. A process as defined in claim 6, wherein hal represents bromine or iodine.

9. A process as defined in claim 6, wherein the organic solvent is selected from the group consisting of aliphatic alkanols from 1 to 4 carbon atoms and halogenated hydrocarbons from 1 to 2 carbon atoms.

10. A pharmaceutical antibacterial composition containing, as the active ingredient, an antibacterial effective amount of a compound as defined in claim 1 in admixture with one or more solid or liquid pharmaceutically acceptable carriers.

11. A pharmaceutical antibacterial composition as defined in claim 10, wherein the active ingredient is 4-deoxy-4'-methyl-pyrido[1',2':1,2]imidazo[4,5-c]rifamycin SV.

12. A pharmaceutical antibacterial composition as defined in claim 10, wherein the active ingredient is 4-deoxy-pyrido[1',2':1,2]imidazo[5,4-c]rifamycin SV.

13. The method of treating antibacterial diseases, which comprises administering to mammals suffering from said disease an antibacterial effective amount of a compound as defined in claim 1.

* * * * *

UNITED STATES PATENT AND TRADEMARK OFFICE
CERTIFICATE OF CORRECTION

PATENT NO. : 4,341,785
DATED : July 27, 1982
INVENTOR(S) : Egidio Marchi, et al.

It is certified that error appears in the above-identified patent and that said Letters Patent are hereby corrected as shown below:

Title page, right column

Column 1, lines 22-40

Column 15, lines 1-20:
 In all three instances, correct the portion of the formula A appearing therein to read:

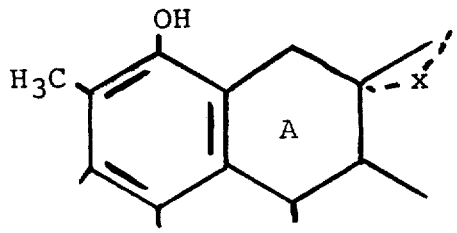

Signed and Sealed this

Twenty-fourth Day of May 1983

[SEAL]

Attest:

DONALD J. QUIGG

Attesting Officer

Acting Commissioner of Patents and Trademarks